(12) United States Patent
Dick et al.

(10) Patent No.: US 9,078,732 B2
(45) Date of Patent: Jul. 14, 2015

(54) OPHTHALMOLOGIC LASER SYSTEM

(75) Inventors: Manfred Dick, Gefell (DE); Matthias Reich, Jena (DE); Dieter Grebner, Grossloebichau (DE)

(73) Assignee: Carl Zeiss Meditec AG, Jena (DE)

( * ) Notice: Subject to any disclaimer, the term of this patent is extended or adjusted under 35 U.S.C. 154(b) by 497 days.

(21) Appl. No.: 13/256,176

(22) PCT Filed: Mar. 11, 2010

(86) PCT No.: PCT/EP2010/001499
§ 371 (c)(1),
(2), (4) Date: Sep. 12, 2011

(87) PCT Pub. No.: WO2010/102804
PCT Pub. Date: Sep. 16, 2010

(65) Prior Publication Data
US 2012/0016352 A1 Jan. 19, 2012

(30) Foreign Application Priority Data
Mar. 12, 2009 (DE) .......................... 10 2009 012 873

(51) Int. Cl.
*A61F 9/008* (2006.01)

(52) U.S. Cl.
CPC .............. *A61F 9/008* (2013.01); *A61F 9/00838* (2013.01); *A61F 2009/0087* (2013.01); *A61F 2009/00872* (2013.01); *A61F 2009/00895* (2013.01); *A61F 2009/00897* (2013.01)

(58) Field of Classification Search
CPC . A61F 9/008; A61F 9/00838; A61F 9/00736; A61F 9/00827; A61F 2009/0087; A61F 2009/00872; A61F 2009/00895; A61F 2009/00897; A61B 2017/00057; A61B 2018/00642; G01N 21/49; G01N 21/64; G01N 21/65; G01N 21/6408

USPC .............................. 606/4–6, 10–12, 107, 166; 351/205–212
See application file for complete search history.

(56) References Cited

U.S. PATENT DOCUMENTS 4,881,808 A * 11/1989 Bille et al. .................... 351/221
6,210,401 B1 4/2001 Lai
(Continued)

FOREIGN PATENT DOCUMENTS

DE 199 40 712 A1 8/1999
DE 101 48 783 A1 9/2001
(Continued)

OTHER PUBLICATIONS

"New Procedure Can Predict Risk of Glare After LASIK" Jan. 2002, 4 pages, https://www.nyee.edu/new-procedure-predicts-risk-of-glare-after-lasik.html.*
(Continued)

*Primary Examiner* — Gary Jackson
*Assistant Examiner* — Boniface N Nganga
(74) *Attorney, Agent, or Firm* — Patterson Thuente Pedersen, P.A.

(57) ABSTRACT

An ophthalmological laser system for photodisruptive irradiation of ocular tissue, including a crystalline lens or a cornea. The system includes an ultra-short pulse laser, the radiation of which is focusable as illumination light via an illumination beam path including a scanner unit and focusing optics. A control unit is programmed to execute determining irradiation control data for photodisruptions at irradiation points in an interior of the ocular tissue distributed three-dimensionally and non-equidistantly to create at least one predetermined target incision. The laser system then irradiates the ocular tissue according to the determined irradiation control data.

20 Claims, 9 Drawing Sheets

(56) References Cited

U.S. PATENT DOCUMENTS

| | | | |
|---|---|---|---|
| 6,478,792 B1* | 11/2002 | Hansel | 606/5 |
| 6,500,171 B1 | 12/2002 | Williams et al. | |
| 6,726,679 B1 | 4/2004 | Dick et al. | |
| 6,902,561 B2 | 6/2005 | Kurtz et al. | |
| 8,425,498 B2 | 4/2013 | Vogler et al. | |
| 2004/0199149 A1 | 10/2004 | Myers et al. | |
| 2006/0155265 A1 | 7/2006 | Juhasz et al. | |
| 2007/0010804 A1* | 1/2007 | Rathjen et al. | 606/5 |
| 2007/0173794 A1* | 7/2007 | Frey et al. | 606/5 |
| 2007/0173795 A1* | 7/2007 | Frey et al. | 606/5 |
| 2007/0185475 A1* | 8/2007 | Frey et al. | 606/4 |
| 2008/0021443 A1* | 1/2008 | Bischoff et al. | 606/5 |
| 2008/0058780 A1* | 3/2008 | Vogler | 606/5 |
| 2008/0249513 A1* | 10/2008 | Vogler et al. | 606/5 |
| 2009/0294422 A1* | 12/2009 | Lubatschowski et al. | 219/121.72 |
| 2010/0004643 A1* | 1/2010 | Frey et al. | 606/5 |

FOREIGN PATENT DOCUMENTS

| | | | |
|---|---|---|---|
| EP | 1 212 022 | 6/2002 | |
| EP | 1 977 725 A1 | 10/2008 | |
| WO | WO 96/11655 | 4/1996 | |
| WO | WO 97/17903 | 5/1997 | |
| WO | WO 01/13838 A1 | 3/2001 | |
| WO | WO 01/35881 A1 | 5/2001 | |
| WO | WO 02/076355 A3 | 10/2002 | |
| WO | WO 03/059563 A2 | 7/2003 | |
| WO | WO 2004/026198 A2 | 4/2004 | |
| WO | WO 2005/070358 A1 | 8/2005 | |
| WO | WO 2007/084627 A2 | 7/2007 | |
| WO | WO 2007084627 A2 * | 7/2007 | A61F 9/008 |
| WO | WO 2007084694 A2 * | 7/2007 | |
| WO | WO 2008/017428 A2 | 2/2008 | |
| WO | WO 2008/064771 A1 | 6/2008 | |

OTHER PUBLICATIONS

"Wavefront Vision Tests" www.nylasik.com Vista Alliance Eye Care Associates, Mar. 2002, 5 pages http://tsdr.uspto.gov/documentviewer?caseId=sn76380600&docId=SPE20080724174544#docIndex=1&page=1.*

Krueger et al., "Rainbow Glare as an Optical Side Effect of Intra Lasik", Ophthalmology, 2008, 115(7).

Roman Grolmus Dissertation, Giessen 2006, VVB Laufersweiler Publishing House.

Schwiegerling, Visual and Ophthalmic Optics, SPIE Press Bellingham, Washington, USA, ISBN 0-8194-5629.

Priest, "The Development of an Average, Anatomically Based, Young Adult, GRIN Eye Model" thesis, (M. Sc.) University of Waterloo, 2004.

Priest, "The Development of an average, anatomically based, young adult, GRIN eye model" thesis (M.Sc.), University of Waterloo, 2004.

Schwiegerling, "Visual and Ophthalmic Optics", SPIE Press Bellingham, Wash. USA, ISBN 0-8194-5629-2.

Dissertation Roman Grolmis, Giessen 2006, VVB Laufersweiler Publishing House.

International Preliminary Report on Patentability for International Application No. PCT/EP2010/001499, dated Sep. 20, 2011.

Schwiegerling, "Visual and Ophthalmic Optics", SPIE Press Bellingham, Wash. USA, ISBN 0-8194-5629-2, Nov. 2004.

Dissertation Roman Grolmis, Glessen 2006, VVB Laufersweiler Publishing House.

German Search Report dated Mar. 12, 2009.

* cited by examiner

OPHTHALMOLOGIC LASER SYSTEM

PRIORITY CLAIM

The present application is a National Phase entry of PCT Application No. PCT/EP2010/001499, filed Mar. 11, 2010, which claims priority from German Application No 102009012873.5, filed Mar. 12, 2009, the disclosures of which are hereby incorporated by reference herein in their entirety.

FIELD OF THE INVENTION

The invention relates to an ophthalmological laser system for the photodisruptive irradiation of ocular tissue, particularly a crystalline lens or a cornea, with a laser, the radiation of which is focusable as illumination light via an illumination beam path, which includes a scanner unit and focusing optics, in an examination region. Furthermore, the invention relates to a method for the photodisruptive irradiation of ocular tissue, particularly a crystalline lens or a cornea, particularly an operating method for an ophthalmological laser system.

BACKGROUND

Accommodation is the ability of the eye to create a sharp image on the retina of an object located at almost any given distance. Thereto, the required adjustment of the refractive power occurs essentially through the elastic deformation of the lens. The possible maximum change in refractive power is called amplitude of accommodation. It can amount to 16 diopters. Due to age-related hardening and/or thickening of the crystalline lens, its amplitude of accommodation decreases. This is called presbyopia or age-related farsightedness. Typically, a crystalline lens is called presbyopic when its amplitude of accommodation drops below 3 diopters. Presbyopia is not a pathological process but a natural sign of old age, starting approximately at age 40. Today, it is principally accepted that a change of the lens substance with continuous growth, i.e., an increase in thickness with age, causes an increase of the lens hardness, therefore constituting a limiting factor of the accommodation. Presumably, the cause for the altered lens elasticity is a sclerosis of the nucleus and the cortex of the crystalline lens.

In ophthalmology it has been suggested to restore improved deformability of a hardened lens through suitable incisions or creation of bubbles by means of a laser surgical therapy, particularly photodisruption (laser-induced optical breakdown or LIOB) or other incisions. Thereby, the accommodative capacity of the lens is to be partially regenerated. In EP 1 212 022 B1 and in US 2004/0199149 A1, such an approach is described using a femtosecond laser.

For example, WO 2005/070358 A1 describes methods for executing different cohesive cut surfaces for producing slip planes. An expanded ophthalmological laser system for presbyopia therapy, e.g., is disclosed in WO 2008/017428. It refers to a navigation apparatus for the optical analysis and processing of the inner structure of the crystalline lens. The navigation apparatus is provided with a confocal detection device. The same laser is provided for the illumination for analyzing of the inner structure as well as for processing. For analysis, the laser light, which is backscattered in the crystalline lens, is detected in order to determine position, geometry, and structure of the crystalline lens. The cutting geometries to be produced during processing are determined with the aid of the detected inner structures and the individual geometric shape of the crystalline lens. For said purpose, a basic model is adjusted to the detected individual geometry. US 2007/0173794 also describes a system for presbyopia therapy, wherein the cut structure is adjusted to the inner lens structure.

Recently, the tightly focused radiation of femtosecond lasers has also been used within the course of an intrastromal keratomileusis (LASIK) in order to produce incisions in the cornea (Femto-LASIK). Such devices are also called laser microkeratomes. Thereby, a photodisruption is produced in the focus, which leads to a minimal formation of bubbles in the stromal tissue. If focal spot is set next to focal spot by means of a scanner system, random incisions (perforations) can be made in the cornea. Such incisions are hereinafter called laser incisions. For example, it is known from US 2006/0155265 A1 to cut the flap by means of a femtosecond laser system. The ablation of the stromal tissue, necessary for a refractive correction, is subsequently executed conservatively by means of an excimer laser, and therefore a mechanical treatment can be completely foregone. In WO 2008/064771 A1, a femtosecond laser system is described which can also prepare the flap but is additionally capable of separating the ablation of stromal tissue, necessary for a refractive correction, through dual incisions for the preparation of a lenticle. This can be called femtosecond lenticle extraction. Subsequently, the lenticle can be removed with a pair of forceps after opening the flap. Therefore, only one laser system is required, the use of an excimer laser can be forgone.

It is problematic that the visual perception can be impaired with all the above-mentioned methods due to a spectral splitting of incidental white light (Krueger, Thornton, Xu, Bor, and van den Berg: "Rainbow Glare as an Optical Side Effect of IntraLasik," Ophthalmology, 2008, 115 (7)). The cause seems to be defect areas which form after the photodisruption through the femtosecond laser at the focal positions and act as transmission dot arrays. The grid structure on the corneal flaps occasionally remains in place. The intensity of the effect can be reduced through the use of focusing optics with greater numerical aperture because smaller disruption bubbles are produced as a result.

SUMMARY OF THE INVENTION

The invention is based on the problem of improving an ophthalmological laser system and an operating method of the initially described type in such a way that the visual perception is less or not at all impaired after treatment.

According to the invention, irradiation control data for photodisruptions at a number of irradiation points in the interior of the ocular tissue by means of at least one predetermined target incision is determined in such a way that the irradiation points are distributed three-dimensionally (particularly along an optical or visual axis) rather than arranged non-equidistantly. In a further step, the ocular tissue is irradiated according to the determined irradiation control data. In other words, the irradiation points are arranged in such a way that non-equidistant distances result from the irradiation between adjacent photodisruption bubbles and particularly between the defect areas resulting from said bubbles. Preferably, this is executed through a control unit by means of an ophthalmological laser system. The three-dimensional distribution and non-equidistant arrangement of the irradiation points can be carried out during the initial generation of irradiation control data or during a subsequent optimization of already generated irradiation control data.

Irradiation control data, according to the invention, are data sets of parameters for a laser device, wherein a corresponding data set is assigned to each irradiation point. Such a single data set, for reasons of simplification, shall hereinafter also be termed irradiation control data. Each data set comprises the coordinates of the corresponding irradiation point, e.g., a coordinates triple (x, y, z,) in the coordinate system of the laser, and preferably an intensity or energy value for the laser pulse to be delivered and optionally a laser pulse frequency.

According to the invention, three-dimensionally distributed signifies that the photodisruption bubbles and the resulting defect areas are not exclusively arranged in one plane. Particularly, the photodisruption bubbles and the resulting defect areas shall not be arranged exclusively in a plane orthogonally arranged to an optical axis (of the laser or the eye) or to a visual axis. Non-equidistant, according to the invention, signifies that a majority of the irradiation points and therefore the photodisruption bubbles to be produced and the resulting defect areas alternatingly exhibit not the same (i.e., different) distances. This shall apply to all three dimensions of the distribution.

Since the irradiation points, at which photodisruptions are to be produced, are, according to the invention, determined specifically in a diffraction-optimized non-equidistant arrangement, diffraction effects can be minimized or avoided similar to an undesirable constructive interference (termed negative interference, according to the invention) in light passing through the ocular tissue. As a result, the visual perception can be improved after treatment with a femtosecond laser.

In the case of a presbyopic crystalline lens as the ocular tissue to be treated, the target incision is, in preferred embodiments, designed for a loosening up of the lens tissue, and so the irradiation control data are (primarily) determined with the objective of loosening up the lens tissue and, according to the invention, are thereby, or subsequently, secondarily optimized for minimal negative interference. In the case of the crystalline lens, the irradiation points are determined in such a way that the laser-supported energy input takes place entirely in the interior of the lens. In the case of a cornea, the target incision is designed for producing a flap and/or a lenticle, and so the irradiation control data are (primarily) determined with the objective of producing a flap and/or a lenticle and, according to the invention, are thereby, or subsequently, secondarily optimized for minimal negative interference. As a result, the visual perception can be improved after laser-supported treatments of the crystalline lens and/or the cornea. Both cases can be combined, wherein the cornea and the lens are treated during the same operation.

Preferably, the irradiation points are arranged regularly because a regular arrangement can be produced with little effort and therefore quickly. Particularly, a first partial quantity of the irradiation points is arranged equidistantly in a first plane lateral to an optical axis, and a second partial quantity of the irradiation points is arranged equidistantly in a second plane lateral to the optical axis, wherein the second plane is separated from the first plane by no more than one diameter of a photodisruption to be produced. With such a regular arrangement of planes staggered in z-direction with their equidistantly arranged irradiation points, a non-equidistant, three-dimensional distribution can be produced with particularly little effort and great speed.

In a particular embodiment, a third partial quantity of the irradiation points is arranged equidistantly in a third plane lateral to the optical axis, wherein the distance to the closer of the two other planes differs from the distance between the two other planes. Thereby, the third plane is advantageously separated from the closer of two other planes by no more than one diameter of a photodisruption to be produced. This efficiently decreases the negative interference.

Alternatively, the irradiation points can also be arranged through statistical distribution. Such a statistical distribution of the irradiation points, e.g., can be derived from a structure, regular in xyz, with equidistant distances in at least one dimension in such a way that, e.g., a Gaussian distribution is allowed for every irradiation point of the applied equidistant grid structure, wherein the full width at half maximum of the Gaussian distribution is, e.g., smaller than the half distance of two irradiation points in the applied grid structure.

This ensures the forming of a cutting plane even though the regularity of the arrangement of the irradiation points was abandoned.

Expediently, the following steps are carried out for determining the irradiation control data:

a) Determination of preliminary irradiation control data in accordance with the at least one target incision;

b) Prediction of an interference pattern resulting from the preliminary irradiation control data with transmitted light;

c) Determination of an intensity of diffraction light of the first or higher order of the predicted interference pattern;

d) Comparison of the determined intensity with a predetermined intensity threshold; and e) Repetition of steps a) to d) if the determined intensity is greater than the intensity threshold, wherein in step a) the preliminary irradiation control data are modified or other preliminary irradiation control data are determined.

Those iterative steps allow for determining diffraction-optimized irradiation control data with little effort and in a short period of time. Expediently, a local maximum (peak) within the relevant diffraction order is determined in step c) and the intensity is used at this juncture for the comparison in step d).

Advantageously, an arrangement for the confocal detection of radiation from the examination region is provided. For example, the detection beam path can be part of a confocal laser scanning microscope (LSM) which is provided in addition to the treatment laser. The confocal detection allows for the measuring of the ocular tissue, particularly its inner properties such as position, form, refractive index distribution, and composition, with great accuracy.

In the case of the cornea, for example, form and/or position of its posterior boundary layer can be determined through confocal detection. The posterior boundary layer is the transition from the endothelium, the posterior border of the cornea, to the aqueous humor of the eye. At said media border, a refractive index jump and an increased reflection occur which, e.g., can be measured with great accuracy with a confocal detector. Alternatively, measuring devices such as a Scheimpflug camera or an OCT system can be used which, however, require more effort. Through the measuring of the posterior boundary layer, it can advantageously be used as reference plane for keratoplastic incisions. In the case of the crystalline lens, form and/or structure and/or position of the crystalline lens can be determined with great accuracy. According to the invention, the position of the crystalline lens comprises the position of the lens as well as its spatial orientation. The information regarding the orientation can also be contained in the form of the crystalline lens. The structure describes the inner configuration of the lens, e.g., inclusions or localized alterations, for example, from age-related tissue modifications or a previous presbyopia therapy.

In a further advantageous embodiment, a beam splitter is provided which channels radiation, which reaches the beam splitter from the direction of the examination region, as detection light through a confocal aperture diaphragm to a detector. This way, the illumination beam path and the detection beam path can be aligned to one another with great accuracy. As a result, the same optical elements (focusing optics, etc.) can be utilized twice. Thereby, embodiments are preferred which, in addition to the illumination laser power, can be adjusted to a surgical therapy laser power. As a result, the same laser can be utilized for the illumination during the determination of form and/or position of the ocular tissue to be treated, as well as for the subsequent treatment, with great positioning accuracy. Thereby, the use of the same laser for measurement and treatment allows for great accuracy in the positioning of the treatment focus since the measurement can be performed in the quasi-absolute reference system of the treatment laser.

Advantageously, the beam splitter is a polarization beam splitter, which decouples the detection light on the detector in such a way that it exhibits a polarization direction different from the emitted illumination light. A large portion of the light, which impinges on the beam splitter from the examination region, originates from reflections on the optical components of the beam path, e.g., the surfaces of the focusing optics; therefore, it exhibits the same polarization direction as the illumination light. Since the beam splitter only directs light as detection light to the detector with a different polarization direction, such stray light is suppressed. However, light backscattered in the cornea or the crystalline lens exhibits an altered polarization direction. Therefore, the detection of the light backscattered in the cornea and/or the crystalline lens is possible with greater accuracy.

In this further embodiment of the invention, irradiation control data for photodisruptions are determined at a plurality of irradiation points in the interior of the ocular tissue by use of at least one predetermined target incision in such a way that the irradiation points are arranged regularly, resulting in a compensation of a refractive deficit through constructive interference in the light passing through the ocular tissue. In a further step, the ocular tissue is irradiated in accordance with the determined irradiation control data. This is preferably carried out through a control unit by an ophthalmological laser system. For example, zones are arranged with irradiation points in accordance with a Fresnel step lens and/or in accordance with a Fresnel zone lens. Preferably, this takes place in addition to a primary irradiation target such as a flap or lenticle incision or a loosening up of a presbyopic crystalline lens.

Since the irradiation points, at which photodisruptions are to be produced, are determined specifically in an interference-producing regular arrangement, inherently unwanted diffraction effects can be used for improving a visual impairment. As a result, particularly an otherwise negative interference can be suppressed. For example, this can be realized in the case of a presbyopic crystalline lens through producing photodisruptions for loosening up of the hardened lens in such a way that specifically resulting diffraction effects compensate a refractive deficit of the eye. From prior art it is only known that artificial intraocular lenses are provided on the surface with refractive and/or diffractive structures (dissertation Roman Grolmus, Giessen 2006, VVB Laufersweiler Publishing House). According to the invention, a corresponding optical effect is achieved. However, according to the invention, said effect is achieved in vivo through photodisruption in the interior of the lens, wherein local refractive index differences between the photodisruption bubbles (cavities) are utilized. The implantation of an artificial intraocular lens can be foregone.

In the case of a presbyopic crystalline lens as the ocular tissue to be treated, the target incision is, in preferred embodiments, designed for a loosening up of the lens tissue, and so the irradiation control data are (primarily) determined with the objective of loosening up the lens tissue and, according to the invention, are thereby, or subsequently, secondarily optimized for minimal negative interference. In the case of the crystalline lens, the irradiation points are determined in such a way that the laser-supported energy input takes place entirely in the interior of the lens. In the case of a cornea, the target incision is designed for producing a flap and/or a lenticle, and so the irradiation control data are (primarily) determined with the objective of producing a flap and/or a lenticle and, according to the invention, are thereby, or subsequently, secondarily optimized for minimal negative interference. As a result, the visual perception can be improved after laser-supported treatments of the crystalline lens and/or the cornea. Both cases can be combined, wherein the cornea and the lens are treated during the same operation.

In preferred embodiments, the irradiation control data are determined in such a way that at least three focal planes result at different distances. This is achieved through a sequential arrangement of interference-producing irradiation point patterns in the manner of a series connection.

In this further embodiment of the invention, irradiation control data for photodisruptions are determined at a plurality of irradiation points in the interior of the ocular tissue by means of at least one predetermined target incision in such a way that different spatial expansions result for at least some of the photodisruptions to be produced. Subsequently, the ocular tissue is irradiated according to the determined irradiation control data. According to the invention, it was realized that interference occurrences can be avoided through varying spatial expansions of the photodisruptions because the defect areas, as scattering centers, exhibit different sizes as a result. This type of diffraction optimization is also applicable for the conventional method of equidistantly arranged irradiation points/photodisruptions/defect areas.

The different spatial expansions can be achieved with little effort, particularly through a variation of a pulse energy between the respective irradiation points and/or through arranging of a varying number of irradiation points for overlapping of the resulting photodisruptions.

The further embodiments described in the following are applicable in embodiments with non-equidistant irradiation points for minimizing interference and in manifestations with regular, specifically refractively and/or diffractively acting, i.e., interference-producing irradiation points.

Preferably, the irradiation points are determined as being positioned on a continuous space curve. Particularly, two consecutive irradiation points can differ in all three spatial coordinates and therefore reduce the radiation exposure. Furthermore, this allows for a completion of the treatment in a short period of time. A control of the x-y-scanners in the form of harmonic oscillations, particularly sine functions, is technically particularly advantageous. This movement can additionally be superimposed with a movement of the irradiation focus in z-direction.

In one embodiment of the invention, at least one property of the ocular tissue is determined before the determination of irradiation control data and taken into account for the determination of the irradiation control data and/or for a correction of the irradiation control data. This allows for great accuracy of the irradiation. For example, the gradient index structure of the crystalline lens as a property can be determined and taken into account. This applies particularly to the equidistant arrangement of irradiation points for the purpose of compensating a visual impairment by means of Fresnel zones or steps.

For such optical determination of properties of the ocular tissue by means of confocal detection, which precedes the generation or correction of irradiation control data, the scan points can be on a continuous space curve. The control of the x-y-scanners, wherein one scanner is controlled with exactly double the frequency than the other scanner, results, e.g., in a Lissajous figure which resembles the FIG. 8. This movement can additionally be superimposed with a movement of the irradiation focus in z-direction. Thereby, two consecutive irradiation points can differ in all three spatial coordinates and therefore reduce the radiation exposure. Furthermore, depending on the motion speed of the focal point of the laser beam, the pulse frequency of the laser light can be adjusted relative to the ocular tissue. As a result, the radiation exposure of the ocular tissue and the eye can be reduced overall during the determination of tissue properties and the actual treatment.

According to one embodiment, an efficiency of the photodisruptive irradiation, position-dependent with regard to the ocular tissue, is taken into account for the determination of the irradiation control data and/or a correction of the irradiation control data. During some examinations it was determined that, particularly depending on the z-position, differences in the interaction between laser radiation and lens tissue occur. Said dependency can be compensated through adjustment of the distances of the irradiation points (spot distance) and the beam energy. As a result, the accuracy of the treatment can be increased. Particularly, the position-dependent efficiency within the course of a corrective step can be taken into account in previously determined irradiation control data.

A non-equidistant arrangement of the irradiation points is preferably produced through spatially non-equidistant control signals by means of a pulse picker, which is arranged before or after a laser amplification arrangement. As a rule, such a pulse picker is already provided before each amplifier stage for the downsampling of the respective input radiation. The frequency of the pulse picker can be varied through an appropriate control in order to adjust the pulse frequency at the laser output in the desired manner. This allows for the adjustment of the distances of the irradiation points with little effort. This can be realized with a modified control of the pulse picker. Generally, the control is effected with a fixed duty cycle, e.g., 99 pulses are blocked in succession and only every hundredth pulse is transmitted. In order to achieve the desired effect, said ratio can be varied, for example, between 80:1 and 120:1. Thereby, the variation can be determined according to the random principle or regularly. The control signals for the pulse picker can, e.g., be determined from the coordinates of two consecutive irradiation points. Advantageously, the pulse energy can also be modulated by means of a pulse picker, wherein the spatial distance between the pulses is adjusted. For example, a higher pulse energy is the result of a greater spatial distance.

The invention also comprises computer programs and control units which are designed for executing a method according to the invention.

BRIEF DESCRIPTION OF THE DRAWINGS

In the following, the invention shall be further explained by means of embodiments.

In all drawings, corresponding parts bear the same legend.

DETAILED DESCRIPTION

Figure 1A:
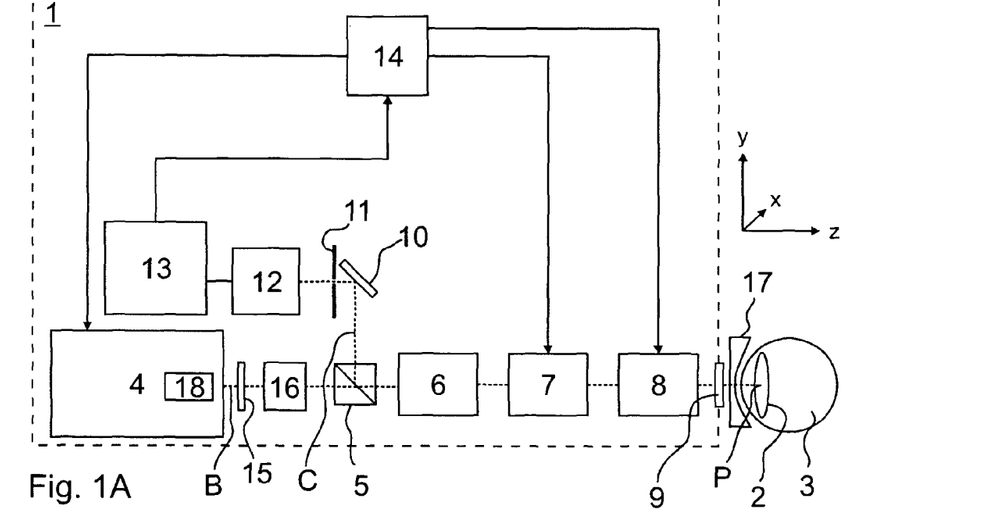
FIG. 1 is a diagram of an ophthalmological laser system for analysis and treatment of the crystalline lens and/or the cornea.
Figure 1B:
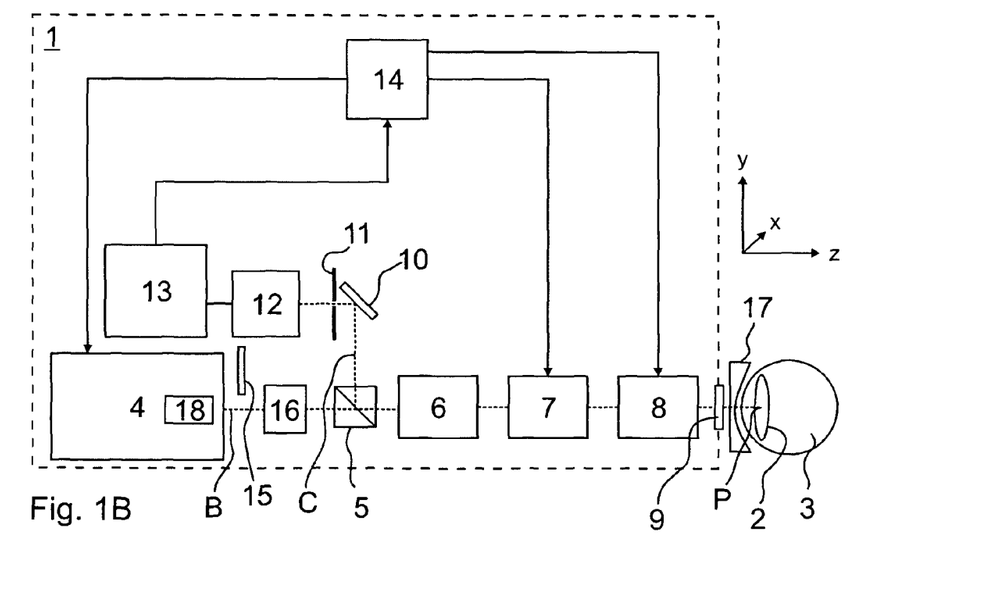

FIG. 1 shows an exemplary ophthalmological laser system 1 for combined analysis and therapy of a presbyopia of a crystalline lens 2 of an eye 3. According to the invention, this system also allows for treatment of the cornea (not depicted) of the eye 3. In the illumination beam path B, the laser system 1 exhibits a laser 4, a polarization beam splitter 5, scan optics 6, a scanner unit 7, focusing optics 8, and an optical phase retardation system 9; a deflection mirror 10, a confocal aperture diaphragm 11, and a detector 12, which form a decoupled detection beam path C; and an amplifier 13 and a control unit 14. In addition, a modulator 16, e.g., an acousto-optical modulator (AOM, AOTF), is provided in the illumination beam path. A contact glass 17 with an immobilization device for the eye 3 is arranged between the laser system 1 and the eye 3 and behind which is the examination region. Other embodiments for the realization of the solution, according to the invention, are possible (not depicted). For example, an independent detection beam path can be used, particularly in the form of a confocal microscope. Thereby, the determination of properties of the tissue to be treated (crystalline lens, cornea) through optical detection does not have to take place in spatial connection with the treatment. It can also take place preoperatively.

For example, the laser 4 is designed as a pulsed TiSa infrared laser with a pulse length between 100 fs and 1000 fs. An attenuator 15 can be tilted into the illumination beam path B. The attenuator 15 is used for switching between an illumination laser power and therapy laser power. Illumination laser power is obtained through the attenuator 15, tilted into the illumination beam path B (partial FIG. 1A), and therapy laser power is obtained without the attenuator 15 (partial FIG. 1B). The optical components, particularly optics 6 and 8, are optimized, corrected, and synchronized towards the objective of a best possible focus miniaturization. For example, its optical aberrations are minimized to a high degree, requiring only a low energy input for a photodisruption. The optical components are designed in such a way that the inherent dispersion of the intraocular media with regard to the change of pulse length as well as the inherent focusing effect of the gradient lens structure of the crystalline lens are pre-compensated. As a result, the size of the focus volume can be maintained constant over the entire area of the crystalline lens and over its entire depth with an error variance of no more than 10%.

The scanner unit 7 comprises, for example, a number of galvanometric mirrors for the deflection of the laser radiation in the x- and y-directions via the crystalline lens 2. The focusing of the laser radiation in z-direction along the optical axis is effected, e.g., through a movable lens or lens group within the scan optics 6 or the focusing optics 8, or alternatively through a movable tube lens (not depicted). The optical phase retardation system 9, for example, is designed as a λ/4 plate, which forms a border of the laser system. The detector 12, e.g., is designed as photomultiplier or as an APD since the light intensities to be mapped are low. The amplifier 13 is designed as a lock-in amplifier and connected to the detector 12 as well as the laser 4. Internally, the laser 4 is equipped with a pulse picker 18 for producing spatially variable distances between consecutive laser pulses. The control unit 14 can adjust the spatial distances through respective control signals.

The pulsed IR laser radiation emerges from the laser 4 and initially passes unchanged through the polarization beam splitter 5. Then it is focused via the scan optics 6, the scanner unit 7, and the focusing optics 8 as illumination light on a scan point P in the crystalline lens 2. Said scan point P can be shifted by means of the scanner unit 7 and a movable lens or lens group within the scan optics 6 or the focusing optics 8 in x-, y-, or z-direction in the crystalline lens 2. Thereby, the optical phase retardation system 9 effects a defined change of the polarization direction of the illumination light passing through.

At the boundary layers of the crystalline lens 2 and the inhomogeneous layers of the crystalline lens (not depicted), a scattering/reflection of the IR radiation occurs, wherein the radiation is partially depolarized in the eye 3. For a treatment of the cornea, this also applies accordingly to the boundary layers and the interior of the cornea. Backscattered/reflected light also impinges on the illumination beam path B and there returns all the way back to the polarization beam splitter 5. The radiation components with unchanged polarization status pass through the polarization beam splitter 5 onto the laser 4. This refers particularly to reflections which originate from the scan optics 6 or the focusing optics 8. Such radiation components, which, after passing through the phase retardation system 9 and/or through depolarization in the eye 3, exhibit a changed polarization status in the crystalline lens 2, are deflected by the polarization beam splitter 5 as detection light into the detection beam path C to the detector 12. The detection light passes via a deflection mirror 10 through the confocal aperture diaphragm 11 onto the detector 12. In another embodiment, the deflection mirror 10 can be omitted or replaced by other beam guidance units. The confocal aperture 11 acts as discriminator in the z-direction, therefore, spatially resolved, only backscattered light is detected from a low focus volume. The control unit 14, through the deflection of the illumination light in x- and y-direction by means of the scanner unit 7 and change of the focusing in z-direction by means of the focusing optics 8, can irradiate random scan points P inside and outside of the crystalline lens 2 with illumination light and determine the strength of the backscatter at said points via the intensity of the corresponding detection light.

In the depicted embodiment, the optical phase retardation system 9 between the eye 3 and focusing optics 8 effects a defined rotation of the polarization direction of the passing illumination light, while stray light, reflected at the optical components, initially maintains the original polarization direction. As a result, the relative intensity of the detection light is increased since the polarization beam splitter 5 separates any light with deviating polarization direction as detection light. In alternative embodiments, the optical phase retardation system 9 can be omitted. Alternatively or additionally, additional polarizers (not depicted) can be positioned in the illumination and/or detection beam path in order to improve the signal quality. In another embodiment, the phase retardation system can be realized as a depolarizer, so that the extent of the phase retardation varies via the beam profile.

Since the signals registered at the detector 12 exhibit a very low intensity, the electronic amplifier is adjusted to an optimized signal-to-noise ratio. An example embodiment is the lock-in amplifier, which is temporally synchronized with the pulse generation and/or the repetition frequency of the laser 2. Other embodiments, for example, utilize so-called boxcar techniques or scanning techniques (sampling) with adding up or averaging. Advantageously, the entire amplifier system of the detector signal exhibits a nonlinear characteristic.

Expediently, the eye 3 of the patient is immobilized prior to a detection and/or therapy, for example, drawn towards a contact glass device 17 by means of a vacuum. In addition, the head of the patient can also be immobilized (not depicted). Through a suitable target (not depicted), the eye position of the patient can be kept as constant as possible. Thereby, an adjustable compensation of the angle between geometry and optical axis of the eye is possible.

For determining the properties of the ocular tissue to be treated (crystalline lens, cornea), the illumination light at illumination laser power (attenuator 15 is positioned in the illumination beam path B) can be guided with a variable pulse frequency across the crystalline lens 2 along an adjustable, continuous, three-dimensional scan curve or structure, wherein detection light is recorded. Thereby, the pulse frequency, in dependence of the speed of the scan movement, is adjusted, e.g., in such a way that a lower pulse frequency results from a slow scan movement than from a fast scan movement. The backscattered detection light is assigned sectionally or pointwise to individual points of the scan curve. Due to the consistency of the scan curve, consecutive scan points differ with regard to all spatial coordinates. From the detected signal values, respective darkfield values are advantageously subtracted, which can be determined in a separate calibration phase.

Figure 2:
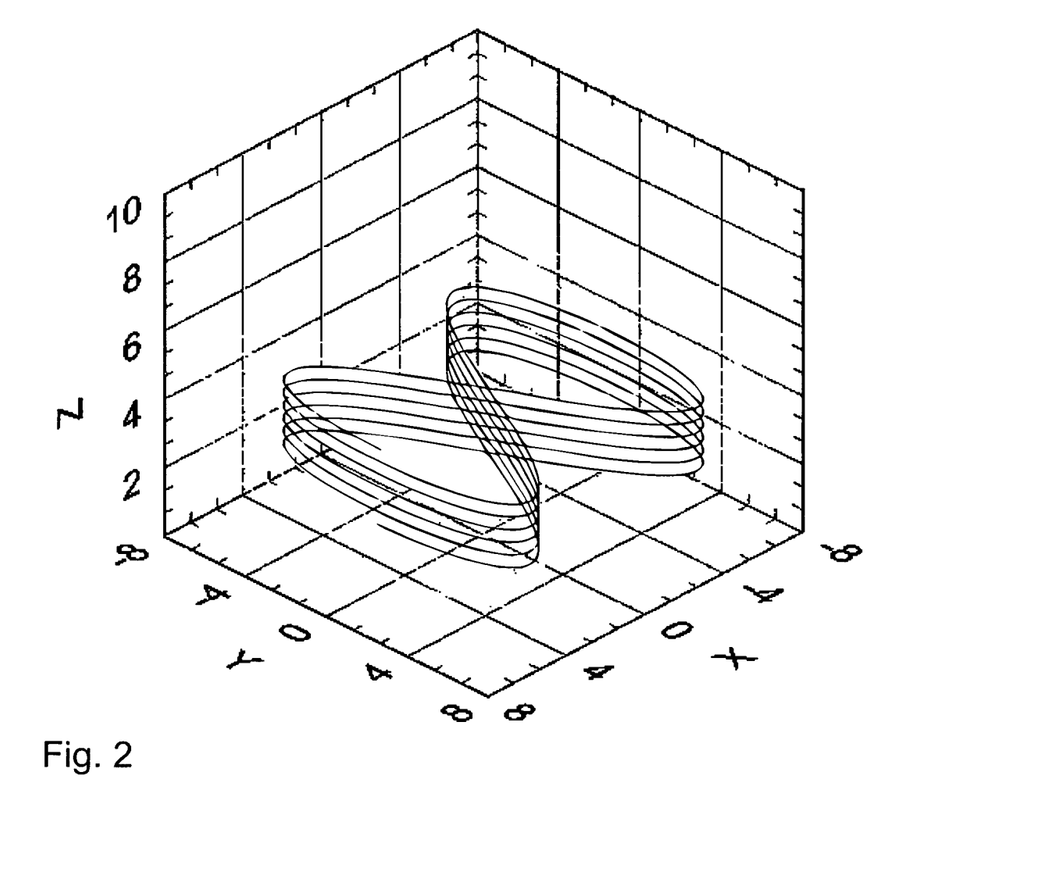
FIG. 2 depicts a space curve for the scanning of the crystalline lens.

FIG. 2 shows an exemplary scan curve in the form of spatially offset figures eights, which can be realized as a Lissajous figure by means of the scanner unit 6. It has the advantage of allowing for the determination of representative data for the reconstruction of a lens model (or the model of a cornea) with great accuracy in a short period of time. Other exemplary forms of scanning and/or rastering can be (not depicted): two crossed rectangles in space; two cylindrical surfaces; a cylindrical body with a profile in the form of a FIG. 8 or 4; several scans along one-dimensional lines. It is also possible to raster the volume of a cylinder or a cube. The volumes and/or surfaces can be scanned continuously or only partially, i.e., with gaps between the individual scan points. As a result, greater distances can occur between individual lines. The scanning structure stretches advantageously from the boundaries via an area from at least 2.5 mm up to 5 mm axially behind the contact glass and from at least 0 mm to 4 mm in diameter laterally with regard to the optical axis of the treatment optics.

Figure 3:
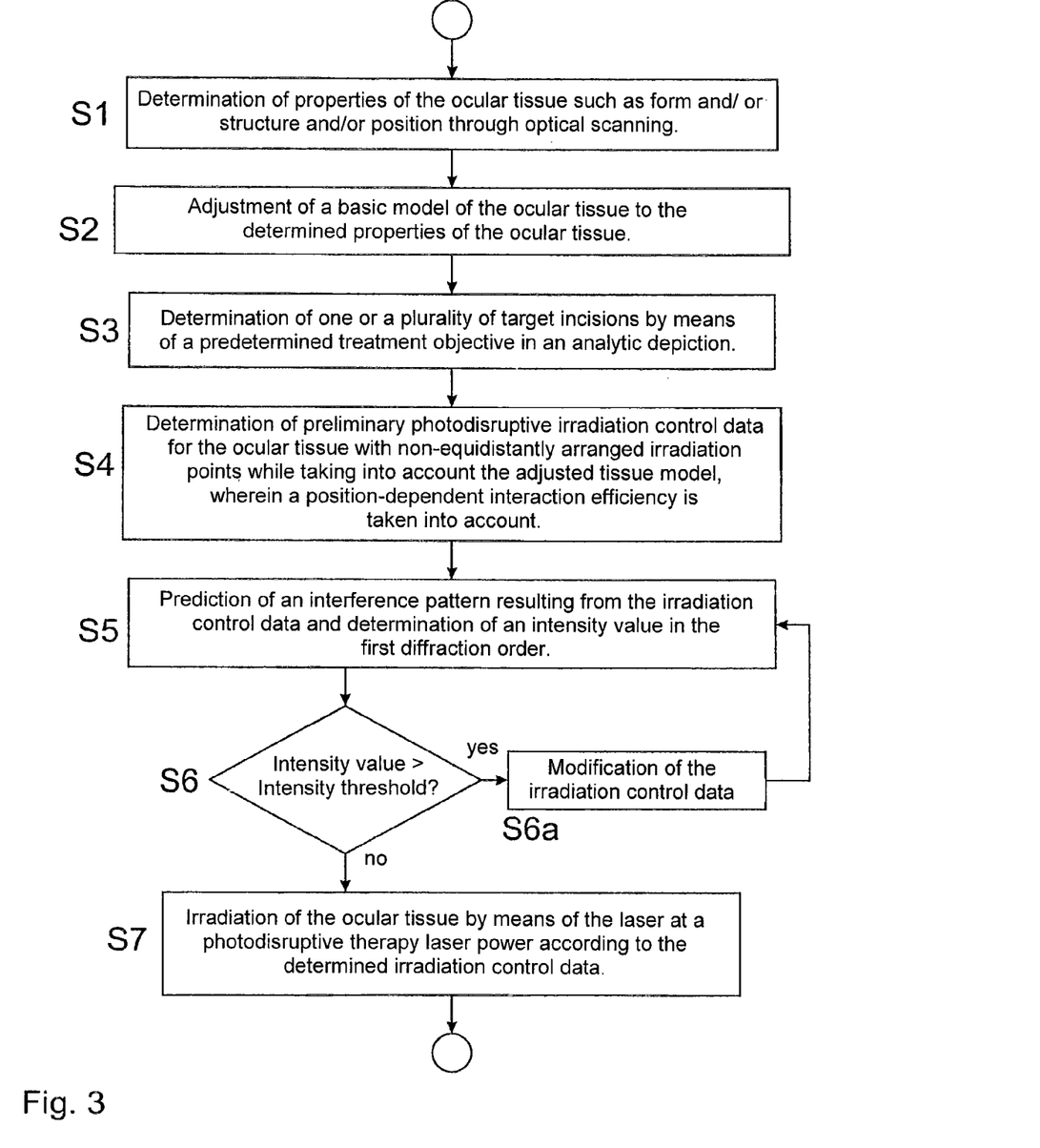
FIG. 3 is a flowchart of an operating method for an ophthalmological system.

The control unit 14 executes, e.g., the operating method as shown in FIG. 3, for the treatment of a presbyopia. Thereby, the same laser 4 is utilized not only for illumination during the detection phase but also for the photodisruption without interposition of the attenuator 15. Particularly, the therapy phase can immediately follow the detection phase. It is also possible to execute the detection phase between the following steps, particularly also repeatedly.

For example, from the intensities assigned to the scan points, form, structure, and the position of the crystalline lens 2 (or the cornea) can be reconstructed (step S1). Thereto, particularly its boundary layers can be identified, e.g., the anterior or posterior boundary layer and/or interior areas such as the junction between cortex and nucleus. Said information is used to adjust a basic model of the crystalline lens (or cornea) to the actual individual condition of the crystalline lens 2 (step S2). For example, basic models can be spherical surfaces, ellipsoids, or conic sections, which are adjusted to the reconstructed properties such as form, structure, and/or position, e.g., through shifting, tilting, clipping of the boundaries, enlargement or stretching in order to allow for a centering with regard to the real position of the lens in space as well as an observance of safety zones. For example, the adjusted model can additionally represent the crystalline lens 2 as a gradient lens, i.e., with an interior course of the refractive index of the lens medium. Particularly, the model can reproduce a tilting of the crystalline lens 2 towards the optical axis of the system 1. In case of the treatment of the cornea, its anterior and/or posterior boundary layer can, e.g., be identified as properties of the ocular tissue for determining the thickness and as reference plane(s).

Using a patient-specifically adjusted model, a number of target incisions are determined (step S3) in accordance with an actual treatment objective, e.g., a loosening up of the crystalline lens (or a flap or lenticle incision in the cornea). This can be effected through the receipt of a manual input by the operator, particularly a physician, or through a computer program in accordance with specifications from the operator. The target incisions, e.g., can be depicted in analytic form, particularly as parameterized functions, and are further processed in this form.

By means of the predetermined target incisions, preliminary, discreet, photodisruptive irradiation control data for the loosening up of the presbyopic crystalline lens 2 with non-equidistantly arranged irradiation points, which are distributed diffraction-optimized, are determined in the known manner (step S4). The irradiation control data, e.g., comprise control signals for the x- and y-axes of the scanner unit and/or for the internal z-focusing, and for the laser beam source and the power modulator 16 as well as the pulse picker 18. For example, for determining the non-equidistant irradiation control data for each target incision, a basic pattern of irradiation points according to type and geometry of the target incision is selected from a predetermined library of diffraction-optimized basic patterns. Every basic pattern contains, e.g, an initial value for a mean distance and a mean scattering of the distances between the irradiation points with which the selection can be made. Furthermore, for every basic pattern, the library contains specifications for possible modification levels for decreasing the negative interference. In addition to basic patterns with parameterized arrangement rules, patterns with random arrangement of the irradiation points can also be used.

Afterwards, the irradiation control data are optimized with regard to the diffraction effect of the resulting defect areas. For this purpose, a simulation is used to predict how strongly an interference pattern would occur with light passing through the ocular tissue if the preliminary irradiation control data were to be transmitted into the tissue (step S5). The strength of the interference pattern is evaluated by means of an intensity maximum in an exemplary first diffraction order and compared with a predetermined maximum intensity threshold (step S6). If the interference intensity is too great, the determination of the irradiation control data is repeated with a higher level of the predetermined modification levels, resulting in a decreased diffraction effect. Within the course of the modification (step S6a), the distances and/or the spatial expansions of the photodisruption bubbles to be produced can be altered. The repetition takes place iteratively until the predetermined maximum intensity threshold in the prognosis is not exceeded.

During the correction for an optimized diffraction effect, the irradiation control data are also adjusted to the position-dependent interaction efficiency with regard to the respective local beam energy and the distances of the irradiation points. Expediently, the irradiation control data can also be corrected by means of the adjusted model of the crystalline lens 2, which represents patient-specific properties of the crystalline lens 2. For said purpose, the patient-specific model can be updated in an intermediate step after a partial determination of the irradiation control data, e.g., as described in FIG. 2, in order to take into account changes of position of the ocular tissue due to temporary eye movements during treatment. This, for example, can also take place repeatedly during the actual irradiation. Thereto, the attenuator 15 is once more temporarily tilted into the illumination beam path B. Expediently, the irradiation control data not yet transmitted into the ocular tissue can then be newly determined by means of the updated model.

Immediately after the determination of the irradiation control data, the actual laser-surgical procedure by means of the irradiation control data is executed with therapy laser power (step S7). Thereby, for example, photodisruption bubbles (cavitation bubbles) with a maximum pulse energy of preferably 0.5 µJ are produced through the laser radiation at a pulse frequency from 100 kHz to 1 MHz and a pulse length of less than 1 ps, particularly 300 fs. As a result, defect areas form with intermediate tissue bands. The diffraction-optimized irradiation control data produce a three-dimensional structure in the crystalline lens which leads to a loosening up of the hardened areas of the crystalline lens, improving the accommodative capacity of the crystalline lens. Through the diffraction-optimized arrangement of the defect areas, the constructive interference is avoided because of the overlapping from the diffraction at the individual defects.

Thereby, the radiation exposure of the retina can be reduced, wherein the therapy is initiated in the posterior area of the crystalline lens 2, e.g., with the rearmost incision, before executing additional therapeutic incisions in the central and anterior area of the crystalline lens 2.

Due to the identical beam path for analysis and therapy, the system 1 is self-calibrating with regard to the viewing position. Since the irradiation control data are determined by means of the information about form/structure/position of the lens, obtained with the identical beam path, the therapy allows for great accuracy.

In an alternative embodiment, preliminary irradiation control data can initially be determined in known fashion from the target incision(s) with conventionally equidistantly arranged irradiation points. Due to the equidistance of the irradiation points, said preliminary irradiation control data would result in an unwanted negative interference if transmitted unaltered into the ocular tissue. According to the invention, the irradiation control data are subsequently diffraction-optimized, wherein the distances between the irradiation points are modified in such a way that they are not arranged non-equidistantly. As described above, the modification can be carried out iteratively.

Figure 4:
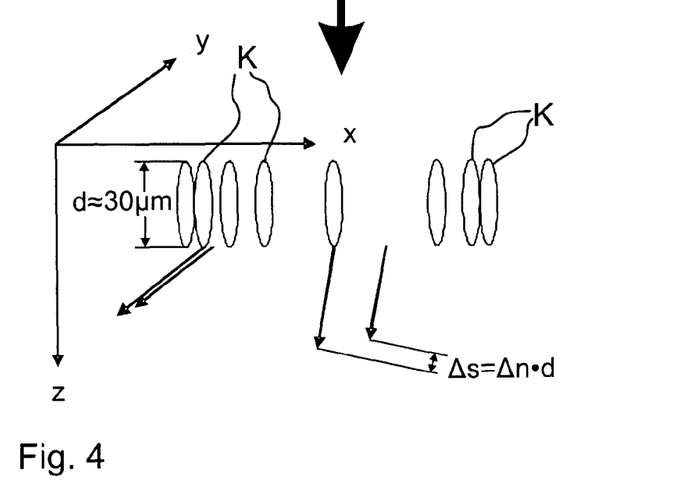
FIG. 4 is a schematic depiction of the principle of operation of a diffraction-optimized arrangement of cavities.

FIG. 4 illustrates the underlying principle of the diffraction-optimization. $\Delta n$ is the refractive index difference between the ocular tissue and the cavity liquid (aqueous humor). Through the non-equidistantly optimized distances between the cavities K, which formed at the irradiation points which lie in one plane, a regular path difference $\Delta s$ is avoided and therefore constructive interference suppressed under the respective local diffraction angles (the narrower the distance, the greater the diffraction angle).

FIG. 5-10 show as schematic cross-sectional view exemplary arrangements of cavities, defect areas and/or cut surfaces which can be produced by means of respective diffraction-optimized irradiation control data for avoiding interference in crystalline lenses 2. As mentioned above, said arrangements can be utilized as basic patterns.

Figure 5A:
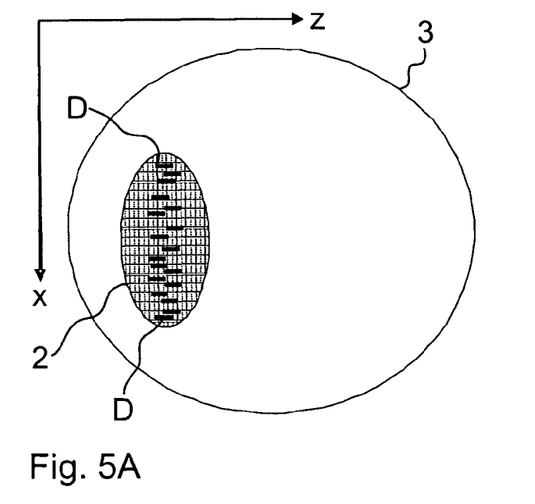
FIG. 5 is a schematic depiction of irregularly arranged defect areas.
Figure 5B:
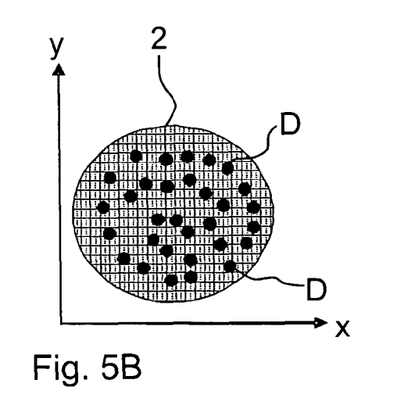

In order to produce defect areas D in accordance with the arrangement in FIG. 5, the irradiation points can, e.g., be arranged on a continuous space curve which runs through such areas of the crystalline lens 2 which are suited for the loosening up of a presbyopia. Thereby, the irradiation points are spaced in such a way that the result is a non-equidistant arrangement of the defect areas D. For example, this can be effected by means of a random number generator, wherein its outputs are used for determining the distances of the irradiation points along the space curve. Alternatively, an initially equidistant arrangement of irradiation points, which are suited for the loosening up of a presbyopic lens, can be diffraction-optimized through subsequent random shuffle of the individual irradiation points, reducing or avoiding negative interference. Expediently, a maximum shuffle width is specified for such a shuffle.

Figure 6A:
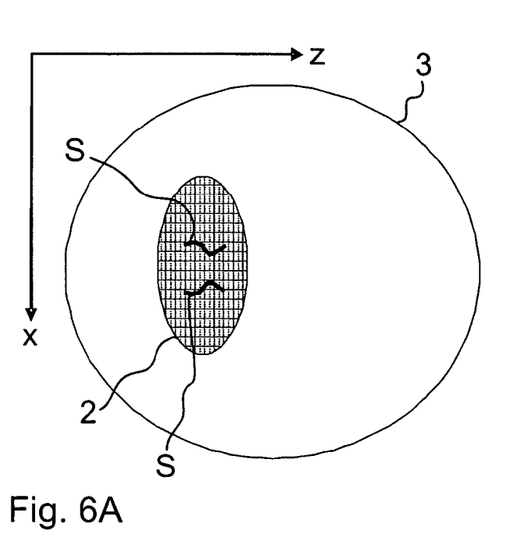
FIG. 6 is a schematic depiction of a first optimized incision arrangement.
Figure 6B:
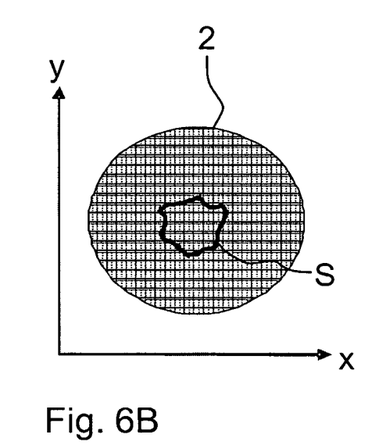
Figure 7A:
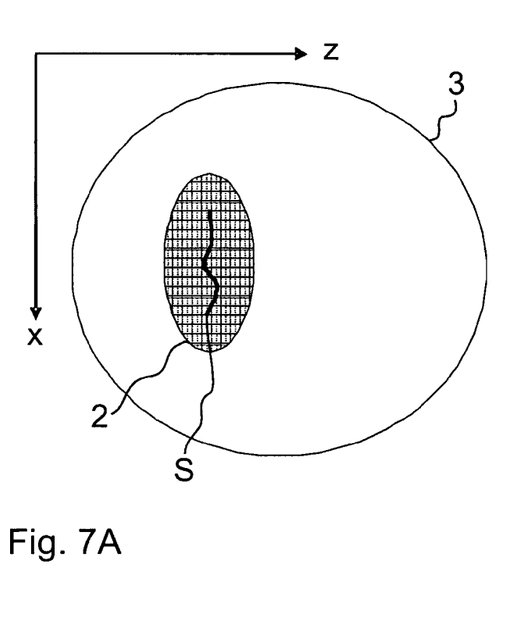
FIG. 7 is a schematic depiction of a second optimized incision arrangement.
Figure 7B:
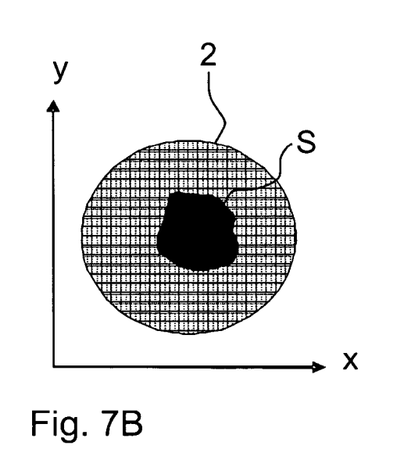

In the embodiment according to FIGS. 6 and 7, the laser radiation is applied in the crystalline lens 2 in such a way that an overlapping occurs between the individual cavities (not depicted). Due to the cohesive line of incision, the forming of isolated defect areas is avoided and the diffraction/interference restricted. The path and the positioning of the photodisruptive incisions produce cut surfaces S which are movable against one another, thereby improving the accommodative capacity of the crystalline lens 2. Through the non-equidistant line of incision in x-, y-, and z-direction, the effect of the structure as a diffractively acting lens is avoided or at least reduced. In FIG. 6, the incisions S are essentially arranged parallel to the optical axis z. In FIG. 7, the incisions S are essentially arranged vertically to the optical axis z.

Figure 8:
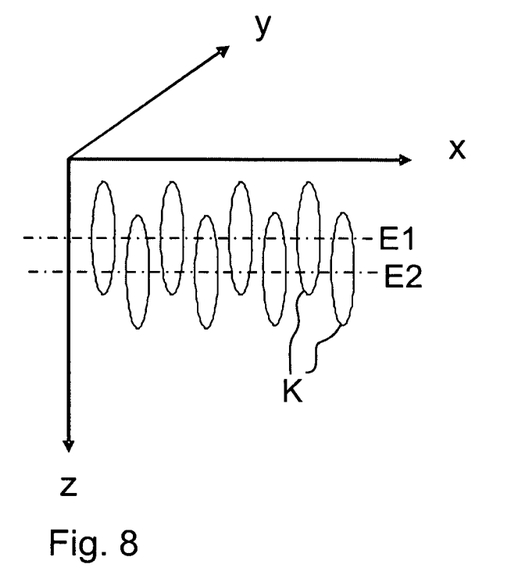
FIG. 8 is a schematic depiction of a first regular non-equidistant arrangement of cavities.

A non-equidistant arrangement of cavities according to FIG. 8 has the advantage that, despite the suppressing of interferences according to the invention, a continuous area of photodisruptions (cut surface) is created with regard to the mechanical effect. The non-equidistant arrangement is achieved through an interlaced arrangement of two planes E1, E2 of irradiation points with corresponding equidistant arrangement within the respective plane while offsetting the planes in z-direction. For example, the two planes E1, E2 can exhibit identical distances between the created cavities K.

Figure 9:
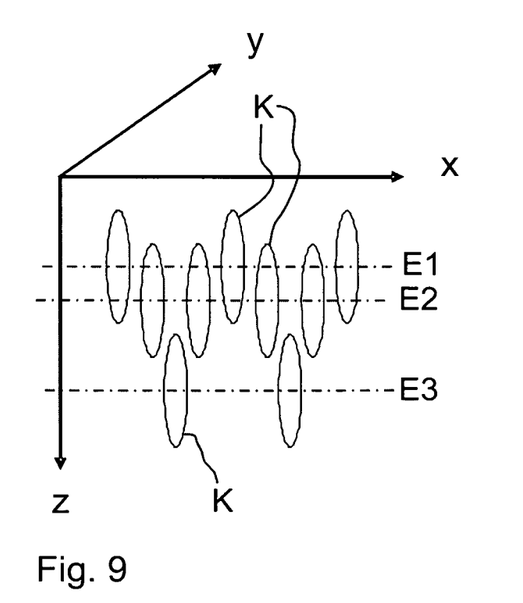
FIG. 9 is a schematic depiction of a second regular non-equidistant arrangement of cavities.

By contrast, the distances between the cavities K within the planes in FIG. 9 are equidistant but differ herein by exhibiting three planes E1, E2, E3. The three planes are arranged with a dual, different offset in z-direction.

In case of basic patterns with a parameterizable rule for arrangement for the irradiation points as shown in FIGS. 8 and 9, modification levels can, e.g., comprise additional planes with irradiation points for a greater suppression of negative interference. Expediently, all planes always exhibit different distances in pairs.

Figure 10:
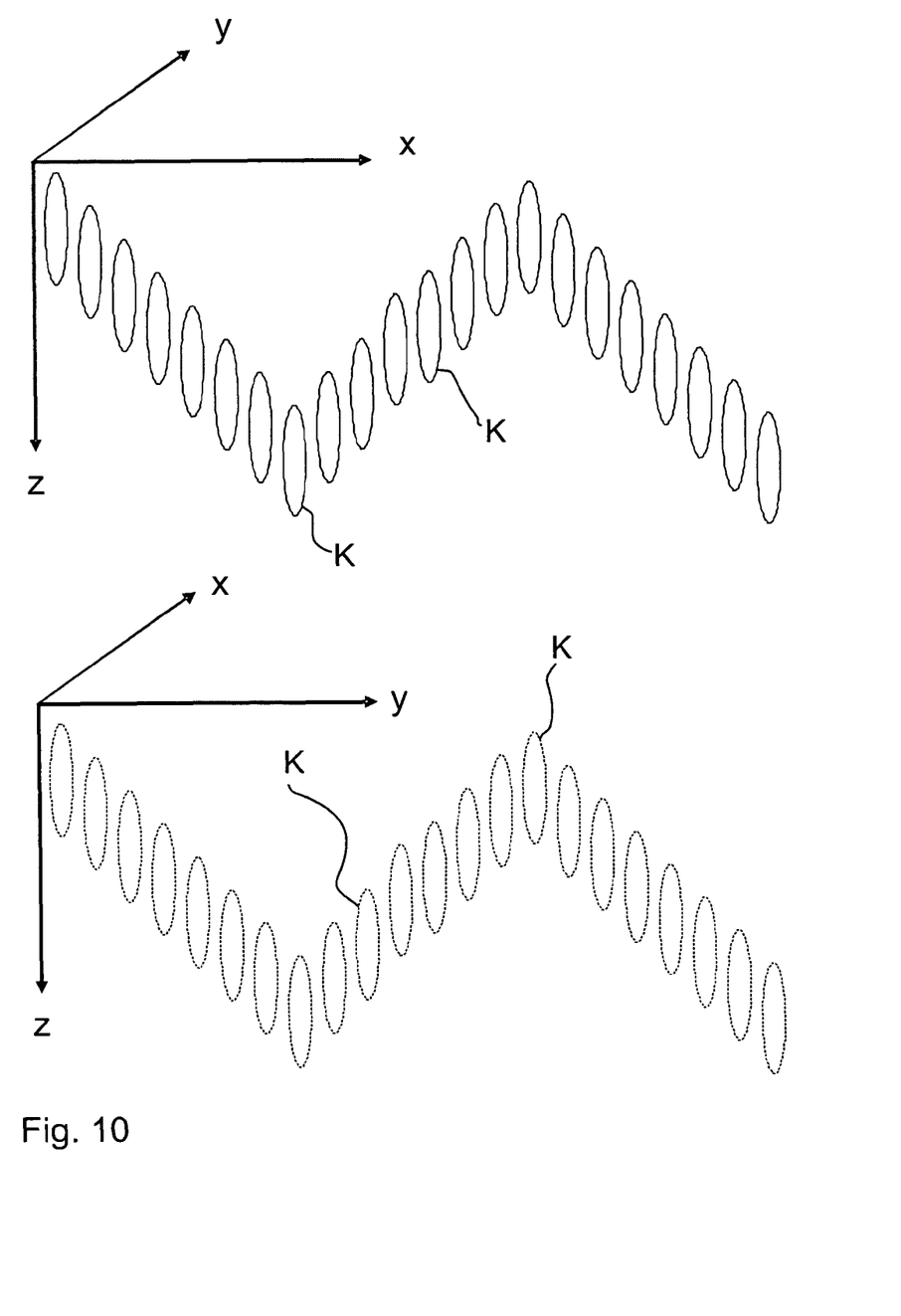
FIG. 10 is a schematic depiction of a third regular non-equidistant arrangement of cavities.

FIG. 10 shows cavities K in a crystalline lens (not depicted) with an equidistant arrangement in x-direction with a multiple equidistant z-offset (above) as well as an optional additional multiple equidistant z-offset (below). Constructive interferences are suppressed through the overall non-equidistant arrangement.

Depending on the spatial position, the distance and/or the applied laser energy between the focal positions can be varied in order to achieve optimal photodisruptions, which are adjusted to the interaction with the ocular tissue (crystalline lens, cornea) to be treated, while substantially avoiding diffraction-induced effects. Furthermore, for the calculation of the irradiation control data, the inner structure of the ocular tissue on the basis of the patient data acquisition and simultaneously the change of the photodisruption efficiency in dependence of the position in x-, y-, and z-direction can additionally be taken into account in all embodiments.

Figure 11:
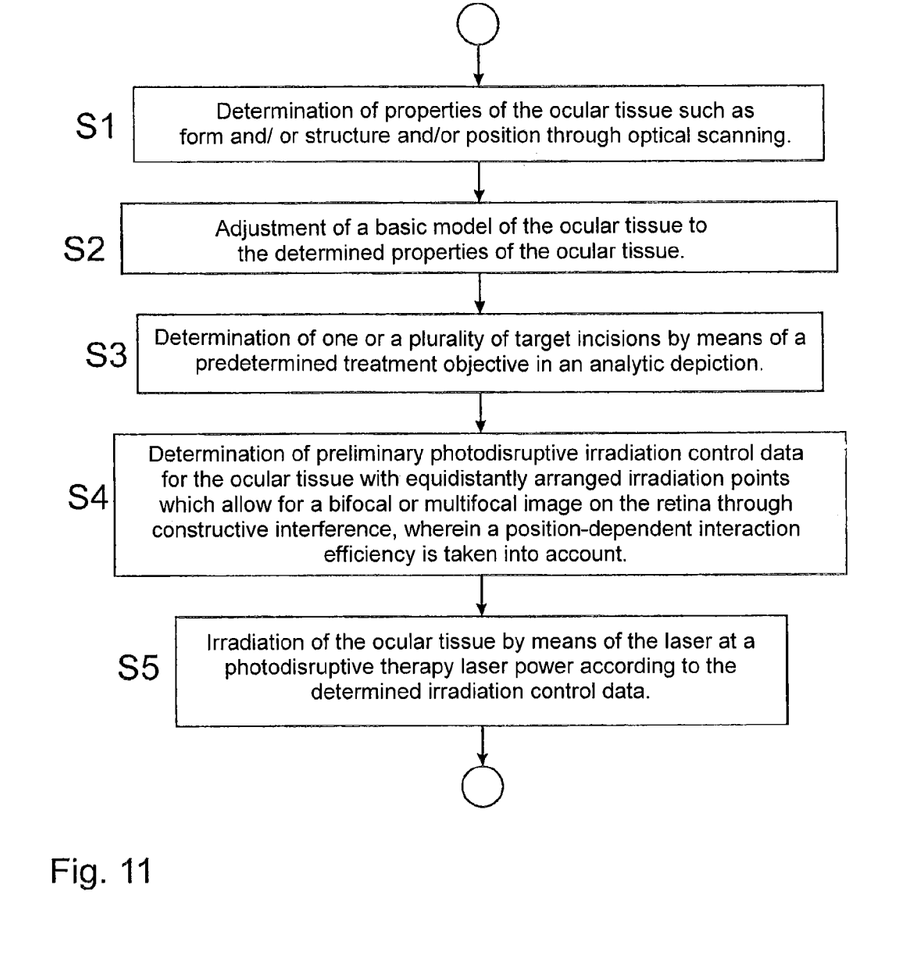
FIG. 11 is a flowchart of a further operating method for an ophthalmological system.

FIG. 11 shows a flowchart for an alternative treatment and operating method. However, in contrast to FIG. 3, three-dimensional and/or two-dimensional structures with a refractive and/or diffractive optical effect which are comprised of disruption bubbles, caused by a femtosecond laser therapy of the presbyopic human eye and/or the cornea through photodisruption, are included in the result in order to compensate for refractive deficits of the eye. In addition to a mechanical tissue loosening, additional optically diffractive or refractive effects can therefore be produced which provide the eye with a bifocal or multifocal function and specifically suppress unwanted optically diffractive or refractive effects such as negative interference.

The introduction of laser spot structures in ocular tissue with the help of a focused ultra-short laser system initially causes the formation of disruption bubbles which fill up with intraocular liquid in a short period of time.

Thereby, it is known that the refractive index of the liquid (water) is generally lower than the refractive index of the tissue, e.g., collagen.

Typical refractive indices within the eye are:
Cornea: $n=1.377$
Aqueous humor: $n=1.337$
Vitreous humor: $n=1.366$
Lens: Gradient lens structure with $n=1.377 \ldots 1.404$
(Jim Schwiegerling: "Visual and Ophthalmic Optics," SPIE Press Bellingham, Wash., USA, ISBN 0-8194-5629-2).

As is evident from the listed data, a refractive index difference of $1.404-1.337=0.067$ within the lens core and of $1.377-1.337=0.04$ within the cornea is to be achieved when locally aqueous-humor-filled cavities are produced. For example, if cavities with a diameter in the order of at least 10 µm are produced, refractive micro-optical structures corresponding to a Fresnel lens structure can be generated. If the diameters of the cavities are smaller than 10 µm (smaller than 1 µm), i.e., in the order of the wavelength of the visual spectrum, diffractive effects corresponding to a Fresnel zone plate can be achieved if corresponding circular structures are produced with regular irradiation point patterns.

In this manner, two-dimensional phase grids can be generated in such a way that they act as a diffractive, focusing or defocusing lens in order to compensate for a visual impairment. For example, this is possible through arrangement in such a way that an image is achieved on the retina through constructive interference. Preferably, a bifocal or multifocal image is produced. Furthermore, the irradiation points can be designed as non-equidistant two-dimensional grid structure in order to introduce mechanical slip planes in the tissue and still suppress unwanted diffraction effects such as negative interference. In addition, three-dimensional phase grids can be generated through the introduction of a plurality of irradiation points positioned at various depths in the manner of a series connection. As a result, a desired diffractive, focusing or defocusing effect can be increased, particularly when equidistant structures are selected.

It is possible in an embodiment of the invention to additionally introduce into the interior of the lens two-dimensional or three-dimensional refractive and/or diffractive lens structures with, e.g., a +3.5 dpt progressive near addition when compared to the lens refractive power, which is responsible for a sharp telephoto, in order to once again make reading possible for presbyopic eyes.

Figure 12:
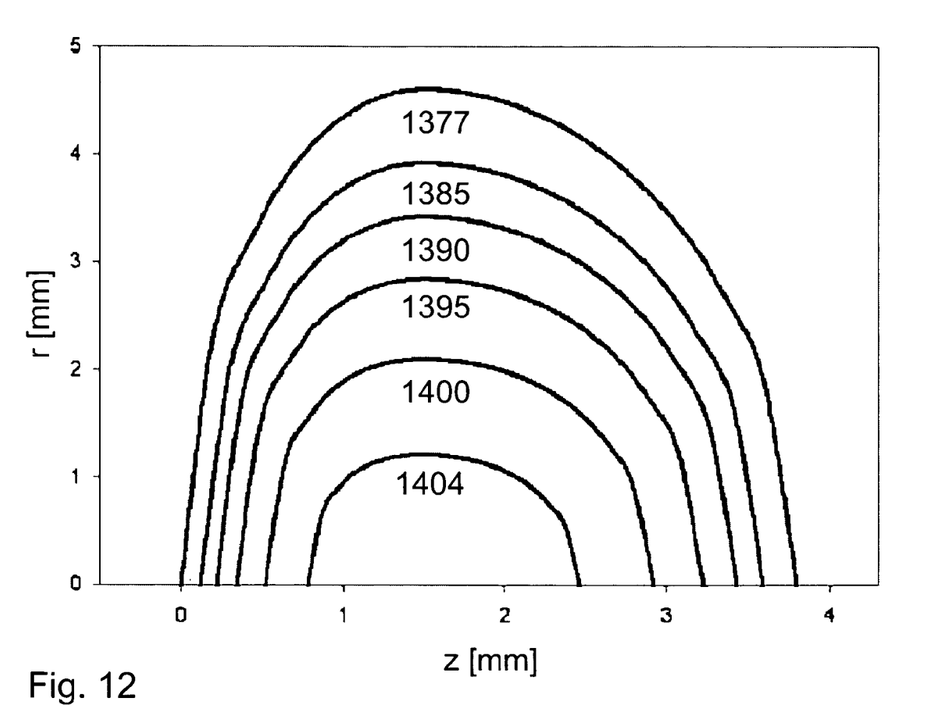
FIG. 12 depicts the inner refractive index gradient of crystalline lenses.

Expediently, the natural gradient lens structure of the human eye, as shown schematically in FIG. 12, is taken into account for the determination of the irradiation control data (A. D. Priest, "The development of an average, anatomically based, young adult, GRIN eye model," thesis, (M.Sc.) University of Waterloo, 2004). Through the introduction of a central, additional diffractive and/or refractive Fresnel lens structure within a day pupil of approximately 2 mm in the central core area of the crystalline lens, it is possible for simplification to proceed by approximation from a homogenous refractive index distribution. However, in case of larger pupillary apertures, the local refractive index differences to the cavities filled with intraocular liquid have to be taken into account individually for great accuracy within the course of a three-dimensional calculation, even if the irradiation points are essentially arranged two-dimensionally in a plane vertical to the optical axis or also visual axis of the eye.

The methods, according to the invention, can also be used with other laser systems. For example, an interferometric measurement of the ocular tissue instead of a confocal detection can be provided for patient data acquisition.

LEGEND

1 Ophthalmological laser system
2 Crystalline lens
3 Eye
4 Laser
5 Beam splitter
6 Scan optics
7 Scanner unit
8 Focusing optics
9 Optical phase retardation system
10 Deflection mirror
11 Confocal aperture diaphragm
12 Detector
13 Amplifier
14 Control unit
15 Attenuator
16 Modulator
17 Immobilization device
18 Pulse picker
B Illumination beam path
C Detection beam path
P Scan point
D Defect
K Cavity
S Cut surface
E1/2/3 Planes of irradiation points

The invention claimed is:

1. An ophthalmological laser system for photodisruptive irradiation of ocular tissue, the ocular tissues including a crystalline lens or a cornea, the ophthalmological laser system comprising:
   an ultra-short pulse laser, the ultra-short pulse laser emitting radiation which is focusable as illumination light via an illumination beam path in an examination region including at least one of the crystalline lens and the cornea, the illumination beam path including a scanner unit and focusing optics;
   a control unit programmed to execute the following:
      determining irradiation control data for photodisruptions at a plurality of irradiation points in an interior of the ocular tissue to create at least one predetermined target incision in such a way that the irradiation points are distributed three-dimensionally and non-equidistantly; and
      irradiating the ocular tissue according to the determined irradiation control data;
      wherein the control unit is further programmed to execute the following to determine the irradiation control data:
         a) determining preliminary irradiation control data in accordance with the at least one target incision;
         b) predicting an interference pattern resulting from the preliminary irradiation control data with transmitted light;
         c) determining an intensity of diffraction light of the first or higher order of the predicted interference pattern;
         d) comparing the determined intensity with a predetermined intensity threshold; and
         e) repetition of a) to d) if the determined intensity is greater than the intensity threshold, wherein in step a) the preliminary irradiation control data are modified or other preliminary irradiation control data are determined.

2. The ophthalmological laser system, according to claim 1, wherein the target incision in the case of the crystalline lens is designed for loosening up of the lens tissue.

3. The ophthalmological laser system, according to claim 1, wherein the target incision in case of the cornea is designed for producing a flap and/or a lenticle.

4. The ophthalmological laser system, according to claim 1, wherein the control unit is further programmed to arrange some irradiation points regularly.

5. The ophthalmological laser system, according to claim 4, wherein the control unit is further programmed to arrange some irradiation points regularly by equidistantly arranging a first partial quantity of the irradiation points in a first plane lateral to an optical axis and equidistantly arranging a second partial quantity of the irradiation points in a second plane lateral to the optical axis, wherein the second plane is separated from the first plane by no more than one diameter of a photodisruption to be produced.

6. The ophthalmological laser system, according to claim 5, wherein the control unit is further programmed to equidistantly arrange a third partial quantity of the irradiation points in a third plane lateral to the optical axis, wherein the distance to the closer of the two other planes differs from the distance between the other two planes.

7. The ophthalmological laser system, according to claim 1, further comprising an arrangement for confocal detection of radiation from the examination region.

8. The ophthalmological laser system, according to claim 1, wherein the control unit is further programmed to execute the following:
   determining irradiation control data for photodisruptions at a plurality of irradiation points in the interior of the ocular tissue to create at least one predetermined target incision in such a way that some of the irradiation points are arranged regularly, to compensate for a refractive deficit through constructive interference in the light passing through the ocular tissue; and
   irradiating the ocular tissue according to the determined irradiation control data.

9. The ophthalmological laser system, according to claim 1, wherein the control unit is further programmed to execute the following:
   determining irradiation control data for photodisruptions at a plurality of irradiation points in the interior of the ocular tissue to create at least one predetermined target incision in such a way that different spatial expansions result for at least some of the photodisruptions to be produced; and irradiating the ocular tissue according to the determined irradiation control data.

10. The ophthalmological laser system according to claim 9, wherein the control unit is further programmed such that the different spatial expansions are statistically distributed.

11. The ophthalmological laser system according to claim 9, wherein the control unit is further programmed such that the different spatial expansions are produced through a variation of a pulse energy between the respective irradiation points and/or through arranging of a varying number of irradiation points for overlapping the resulting photodisruptions.

12. The ophthalmological laser system according to claim 1, wherein at least one property of the ocular tissue is determined before the determination of the irradiation control data and taken into account for the determination of the irradiation control data and/or for correction of the irradiation control data.

13. The ophthalmological laser system according to claim 1, wherein efficiency of the photodisruptive irradiation is position-dependent with regard to the ocular tissue and wherein the efficiency of the photodisruptive irradiation is taken into account in the determination of the irradiation control data and/or correction of the irradiation control data.

14. The ophthalmological laser system according to claim 1, wherein a non-equidistant arrangement of the irradiation points is produced through spatially non-equidistant control signals by a pulse picker, the pulse picker being arranged before or after a laser amplification arrangement of the ophthalmological laser system.

15. A method for photodisruptive treatment of ocular tissue, including a crystalline lens or a cornea, the method comprising:

determining irradiation control data by application of a programmed control unit for photodisruptions at a plurality of irradiation points in the interior of the ocular tissue to create at least one predetermined target incision, such that the irradiation points are distributed three-dimensionally and non-equidistantly within the crystalline lens or cornea; and irradiating the ocular tissue according to the determined irradiation control data by application of ultra-short laser pulses from an ultra-short pulse laser, scanner unit and focusing optics, the ultra-short pulse laser, scanner unit and focusing optics being operably coupled to and controlled by the programmed control unit;

wherein determining irradiation control data by application of the programmed control unit further comprises:
a) determining preliminary irradiation control data in accordance with the at least one target incision;
b) predicting an interference pattern resulting from the preliminary irradiation control data with transmitted light;
c) determining an intensity of diffraction light of the first or higher order of the predicted interference pattern;
d) comparing the determined intensity with a predetermined intensity threshold; and
e) repetition of a) to d) if the determined intensity is greater than the intensity threshold, wherein in step a) the preliminary irradiation control data are modified or other preliminary irradiation control data are determined.

16. The method for the photodisruptive treatment of ocular tissue, according to claim 15, comprising:

determining the irradiation control data for the photodisruptions at the plurality of irradiation points in the interior of the ocular tissue to create at least one predetermined target incision in such a way that different spatial expansions are resulting for at least some of the photodisruptions to be produced; and irradiating according to the determined irradiation control data.

17. The method for the photodisruptive treatment of ocular tissue, according to claim 16, further comprising distributing the different spatial expansions statistically.

18. The method for the photodisruptive treatment of ocular tissue, according to claim 15, further comprising determining at least one property of the ocular tissue before the determination of irradiation control data and taking the at least one property into account for the determination of the irradiation control data and/or for a correction of the irradiation control data.

19. The method for the photodisruptive treatment of ocular tissue, according to claim 15, further comprising taking into account an efficiency of the photodisruptive irradiation, on a position-dependent basis with regard to the ocular tissue for the determination of the irradiation control data and/or a correction of the irradiation control data.

20. The method of the photodisruptive treatment of ocular tissue, according to claim 15, further comprising producing a non-equidistant arrangement of the irradiation points through spatially non-equidistant control signals by application of a pulse picker, the pulse picker being arranged before or after a laser amplification arrangement of the ophthalmological laser system.

* * * * *